US012049768B2

(12) United States Patent
Gong (10) Patent No.: US 12,049,768 B2
(45) Date of Patent: Jul. 30, 2024

(54) WATER PURIFICATION, STERILIZATION AND DISINFECTION LAMP

(71) Applicant: SHEN ZHEN LAMHO PHOTOELECTRICITY & TECHNOLOGY CO., LTD, Shenzhen (CN)

(72) Inventor: Yelin Gong, Fuzhou (CN)

(73) Assignee: SHEN ZHEN LAMHO PHOTOELECTRICITY & TECHNOLOGY CO., LTD, Shenzhen (CN)

( * ) Notice: Subject to any disclaimer, the term of this patent is extended or adjusted under 35 U.S.C. 154(b) by 0 days.

(21) Appl. No.: 18/407,456

(22) Filed: Jan. 9, 2024

(65) Prior Publication Data

US 2024/0141666 A1    May 2, 2024

(51) Int. Cl.
*E04H 4/14* (2006.01)
*A61L 2/08* (2006.01)
*A61L 2/23* (2006.01)
*C02F 1/68* (2023.01)
*E04H 4/12* (2006.01)
*F21S 9/03* (2006.01)
(Continued)

(52) U.S. Cl.
CPC ............... *E04H 4/148* (2013.01); *A61L 2/08* (2013.01); *A61L 2/23* (2013.01); *C02F 1/687* (2013.01); *E04H 4/1209* (2013.01); *E04H 4/14* (2013.01); *F21S 9/03* (2013.01); *F21V 33/00* (2013.01); *H01L 31/00* (2013.01); *H01L 31/0203* (2013.01); *H01L 31/048* (2013.01); *C02F 2103/42* (2013.01); *C02F 2201/002* (2013.01)

(58) Field of Classification Search
CPC ............... C02F 1/687; C02F 2103/42; C02F 2201/002; A61L 2/08; A61L 2/23; E04H 4/1209; E04H 4/14; E04H 4/148; F21S 9/03; F21V 33/00; H01L 31/00; H01L 31/0203; H01L 31/048
See application file for complete search history.

(56) References Cited

U.S. PATENT DOCUMENTS

2015/0021243 A1 * 1/2015 Herrington ........... C02F 1/4672
  210/85
2018/0055960 A1 * 3/2018 Reiber ..................... A61L 2/10
(Continued)

FOREIGN PATENT DOCUMENTS

CN        205773554 U  * 12/2016
WO   WO-2019099034 A1 * 5/2019

OTHER PUBLICATIONS

English translation Chinese Patent Application No. 205773554 U (2016).*

*Primary Examiner* — John Kim
(74) *Attorney, Agent, or Firm* — Zhigang Ma (57) ABSTRACT

Disclosed is a water purification, sterilization and disinfection lamp. The lamp includes a lampshade, a base and a cylinder for storing slow-release chlorine tablets. A circuit board and a battery electrically connected with the circuit board are arranged on the base. A solar panel is installed on a surface of the lampshade. The base is covered with the lampshade to form sealed connection. The solar panel is electrically connected with the circuit board. At least one lamp bead is assembled on the circuit board. The irradiation direction of the lamp bead faces the direction of the lampshade.

10 Claims, 9 Drawing Sheets

(51) Int. Cl.
  *F21V 33/00* (2006.01)
  *H01L 31/00* (2006.01)
  *H01L 31/02* (2006.01)
  *H01L 31/0203* (2014.01)
  *H01L 31/04* (2014.01)
  *H01L 31/048* (2014.01)
  *C02F 103/42* (2006.01)

(56) References Cited

U.S. PATENT DOCUMENTS

2018/0215634 A1   8/2018   Jung et al.
2020/0172413 A1   6/2020   Jung et al.
2022/0135441 A1   5/2022   Jung et al.

* cited by examiner

WATER PURIFICATION, STERILIZATION AND DISINFECTION LAMP

TECHNICAL FIELD

The present disclosure relates to the technical field of swimming pool sterilization devices, in particular to a water purification, sterilization and disinfection lamp.

BACKGROUND

As we all know, the swimming pool is a special place for people to swim. However, in order to be clean and hygienic, water in the swimming pool needs to be purified, sterilized and disinfected regularly to ensure the water sanitation of the swimming pool. In general, when water in the swimming pool is purified, bacteriocidal substances, such as slow-release chlorine tablets, are generally put into water. The slow-release chlorine tablets are slowly dissolved in the water to play a role in sterilization and disinfection.

When the slow-release chlorine tablets are used, in order to improve the attractive appearance and cleanliness of the swimming pool, the slow-release chlorine tablets are generally not directly thrown into the swimming pool, but are accommodated in some devices, such as chlorine buoys, and then the devices are put into the water. However, the existing devices are only used to accommodate chlorine tablets and float on the water surface, but do not have other functions. For example, the attractive appearance is not promoted, on the contrary, the attractive appearance of the swimming pool is affected, and the overall product experience of the user is low.

SUMMARY

Aiming at the shortages in the prior art, the present disclosure aims to provide a water purification, sterilization and disinfection lamp.

In order to achieve the above purpose, the present disclosure adopts the following technical scheme.

A water purification, sterilization and disinfection lamp includes a lampshade, a base and a cylinder for storing slow-release chlorine tablets. A circuit board and a battery electrically connected with the circuit board are arranged on the base. A solar panel is installed on a surface of the lampshade. The base is covered with the lampshade to form sealed connection. The solar panel is electrically connected with the circuit board. At least one lamp bead is assembled on the circuit board. The irradiation direction of the lamp bead faces the direction of the lampshade. The cylinder is detachably installed at the bottom of the base. Permeable holes are formed in the cylinder. The slow-release chlorine tablets are in contact with the water through the permeable holes in the cylinder.

Preferably, the lamp also includes an infrared remote controller. The circuit board is integrated with infrared receiving modules for receiving infrared remote control information. At least two infrared receiving modules are respectively located at both ends of the circuit board.

Preferably, at least two protrusions are arranged at the end, located at a cavity opening, of the cylinder. A mating slot capable of accommodating one end of the cylinder to be inserted into is arranged at the bottom of the base. An L-shaped slot is formed in a slot wall of the mating slot. An end of the cylinder is inserted into the mating slot. The protrusions are locked into the slot by rotation.

Preferably, the cylinder includes two semi-cylinders. The semi-cylinders are connected through a bending part. The other ends of the semi-cylinders are connected through buckles respectively.

Preferably, lower ends of the semi-cylinder are in sleeve joint with a cover body. Avoidance holes, located at the permeable holes, are formed in the cover body.

Preferably, an annular floating block sleeves the cylinder. An upper end of the floating block abuts against the bottom of the base.

Preferably, the floating block is PE (polyethylene) foam.

Preferably, the lamp bead is a colorful RGB (Red Green Blue) lamp bead.

Preferably, a surface of the lampshade is provided with diamond lines.

Preferably, the circuit board is provided with buttons. The button is a waterproof button. A button cap of the button is placed in the mating slot of the base.

Due to the adoption of the scheme, the lamp can float on a surface of water, and the cylinder loaded with the slow-release chlorine tablets is soaked in the water to achieve the conventional functions of purifying, sterilizing and disinfecting water. The part floating on the surface of water is designed in an integrated way to strengthen the waterproof performance, and the functions of lighting effect, solar power generation and wireless infrared remote control are added, so that the functional diversity of the product is improved in many aspects, and more dazzling visual senses can be provided to bring better product experience to users when the water is purified.

DETAILED DESCRIPTION OF THE EMBODIMENTS

In order to make the objectives, technical solutions and advantages of the present disclosure clearer, the present disclosure will be further described with reference to the attached figures and embodiments thereof. It shall be understood that, the embodiments described herein are only intended to illustrate but not to limit the present disclosure.

In the description of the present disclosure, it needs to be illustrated that the indicative direction or position relations of the terms such as "center", "longitudinal", "transverse", "length", "width", "thickness", "upper", "lower", "front", "rear", "left", "right", "vertical", "horizontal", "top", "bottom", "inside", "outside", "clockwise" and "anti-clockwise" are direction or position relations illustrated based on the attached figures, just for facilitating the description of the present disclosure and simplifying the description, but not for indicating or hinting that the indicated device or element must be in a specific direction and is constructed and operated in the specific direction, the terms cannot be understood as the restriction of the present disclosure. In addition, the terms "first" and "second" are merely intended for a purpose of description, and shall not be understood as an indication or implication of relative importance or implicit indication of the number of indicated technical features. Therefore, a feature limited by "first" or "second" may include one or more features explicitly or implicitly. In the description of the present disclosure, the meaning of "a plurality of" means two or more unless expressly specifically defined otherwise.

In the description of the present disclosure, it should be noted that, unless expressly specified and limited otherwise, the terms "installed", "linked", "connected" and "arranged" are to be understood broadly and, for example, may be fixedly connected, arranged, or may be detachably connected, arranged, or integrally connected, arranged. The components can be mechanically connected or electrically connected. The components can be directly connected and also can be indirectly connected through an intermediate, and two components can be communicated internally or interact with each other. For those skilled in the art, the specific meanings of the terms in the present disclosure can be understood according to specific conditions.

As shown in FIG. 1 to FIG. 9, a water purification, sterilization and disinfection lamp provided by the embodiment includes a lampshade 1, a base 2 and a cylinder 3 for storing slow-release chlorine tablets 100. A circuit board 21 and a battery 22 electrically connected with the circuit board 21 are arranged on the base 2. A solar panel 11 is installed on a surface of the lampshade 1. The base 2 is covered with the lampshade 1 to form sealed connection without a waterproof ring by ultrasonic welding. The waterproof performance is more stable, and the aging resistance is also relatively high. The solar panel 11 is electrically connected with the circuit board 21. At least one lamp bead 23 is assembled on the circuit board 21. The irradiation direction of the lamp bead 23 faces the direction of the lampshade 1. The cylinder 3 is detachably installed at the bottom of the base 2, and permeable holes 31 are formed in the cylinder 3. The slow-release chlorine tablets 100 are in contact with the water through the permeable holes 31 in the cylinder 3.

According to the embodiment, the lamp can float on a surface of water, and the cylinder 3 loaded with the slow-release chlorine tablets 100 is soaked in the water to achieve the conventional functions of purifying, sterilizing and disinfecting water. The part floating on the surface of water is designed in an integrated way to strengthen the waterproof performance, and the functions of lighting effect and solar power generation are added, so that the functional diversity of the product is improved in many aspects, and more dazzling visual senses can be provided to bring better product experience to users when the water is purified. Wherein, depending on the setting of lamplight, corresponding lamplight can be emitted on a water surface after the lamp bead 23 is turned on. Especially when the water is purified at night, a very beautiful scene can be given for a swimming pool to add an aesthetic feeling of the environment. When the solar panel 11 generates electricity, the internal battery 22 can be charged when there is sunlight, so that the lamp bead 23 can emit light, manual charging of the product is omitted, and the convenience is improved.

In specific use, the slow-release chlorine tablets 100 need to be put into the cylinder 3 one by one, then the cylinder 3 is installed on the base 2, and then the slow-release chlorine tablets 100 can be directly put into water. Water can be gradually introduced into the cylinder 3 through the permeable holes 31 formed in the cylinder 3 to be in contact with the slow-release chlorine tablets 100, so that the water in the swimming pool is purified. In the purification process, the lamp bead 23 can be turned on to refract the light of the lamp bead 23 from the lampshade 1. Internal electric energy is mainly provided by the battery 22, and the charging of the battery 22 depends on the solar panel 11 arranged outside the lampshade for solar power generation. Because the solar panel 11 is directly arranged outside the lampshade 1, some materials such as the lampshade 1 can be prevented from shielding sunlight, so that more light energy can be converted into electric energy. When the slow-release chlorine tablets 100 in the cylinder 3 are used up, the cylinder 3 can be directly disassembled, new slow-release chlorine tablets 100 are put into the cylinder 3, and then the cylinder 3 continues to be used.

Further, in order to conveniently control the operation of the lamp bead 23, the embodiment also includes an infrared remote controller. The circuit board 21 is integrated with infrared receiving modules 24 for receiving infrared remote control information. At least two infrared receiving modules 24 are respectively located at both ends of the circuit board 21, so that remote control can be carried out at 360 degrees without dead angle. The structure of an overall circuit diagram is shown in FIG. 6 to FIG. 9. For infrared remote control, received remote control waveforms are decoded through two IO (Input/Output) ports (chip pins), and the same signal processing is carried out on two groups of data decoded simultaneously within an interval of 0.1 s to avoid misoperation. Therefore, the user can control and regulate the lamp bead 23 through the infrared remote controller. For example, the lamp bead 23 is turned on and turned off, and the lamplight is brightened and dark, flashed and timed. Color change can be controlled when the lamp bead 23 is a colorful RGB lamp bead selectively. The overall control method can be defined to be various, and the flashing modes are various, so there will be more choices in use.

Further, the cylinder 3 and the base 2 are detachably installed. Therefore, in the embodiment, at least two protrusions 32 are arranged at the end, located at a cavity opening, of the cylinder 3. A mating slot 25 capable of accommodating one end of the cylinder 3 to be inserted into is arranged at the bottom of the base 2. An L-shaped slot 26 is formed in a slot wall of the mating slot 25. An end of the cylinder 3 is inserted into the mating slot 25, and the protrusions 32 are locked into the slot 26 by rotation. Therefore, detachable installation of the cylinder 3 and the base 2 is achieved.

Figure 1:
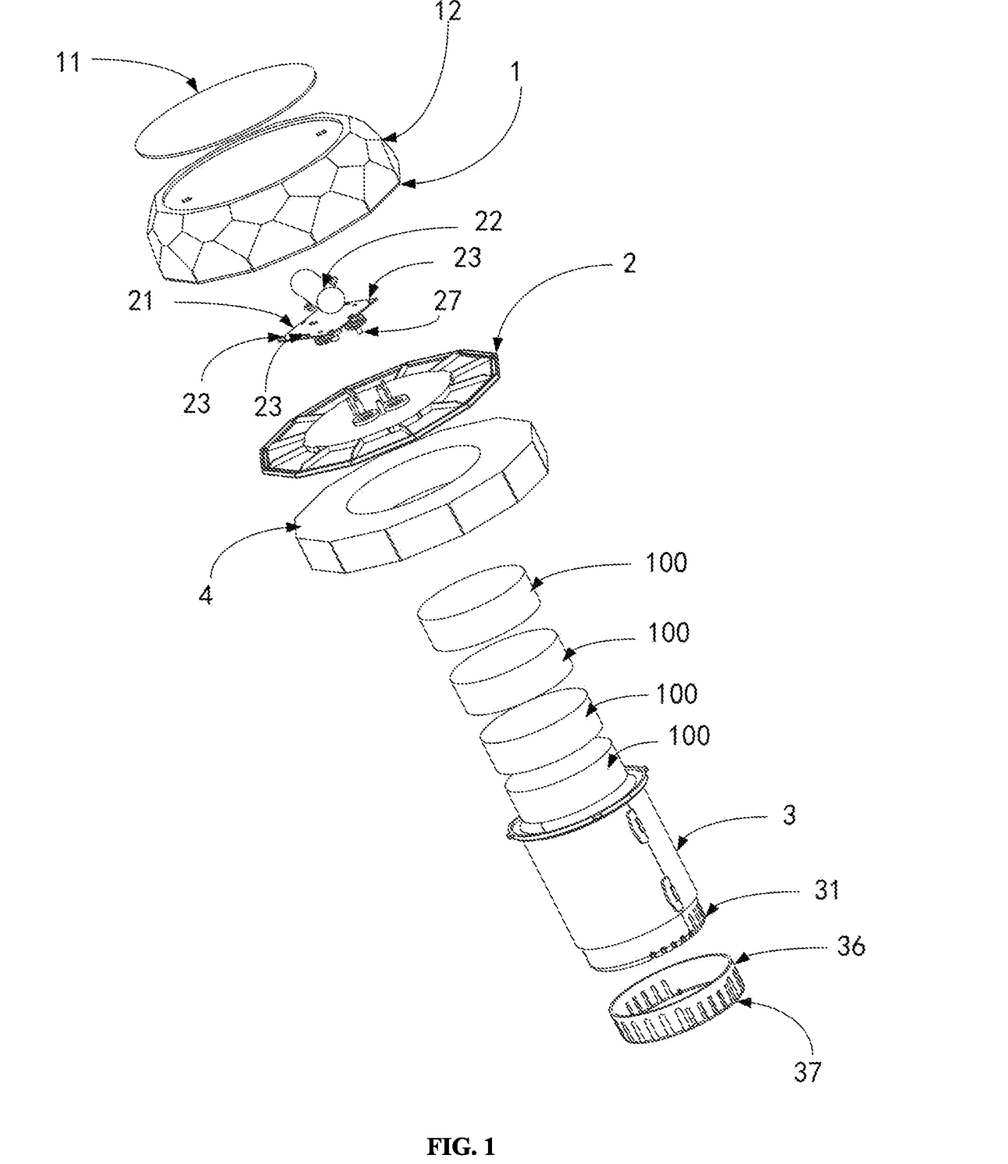
FIG. 1 is a structural exploded view in the embodiment of the present disclosure.
Figure 2:
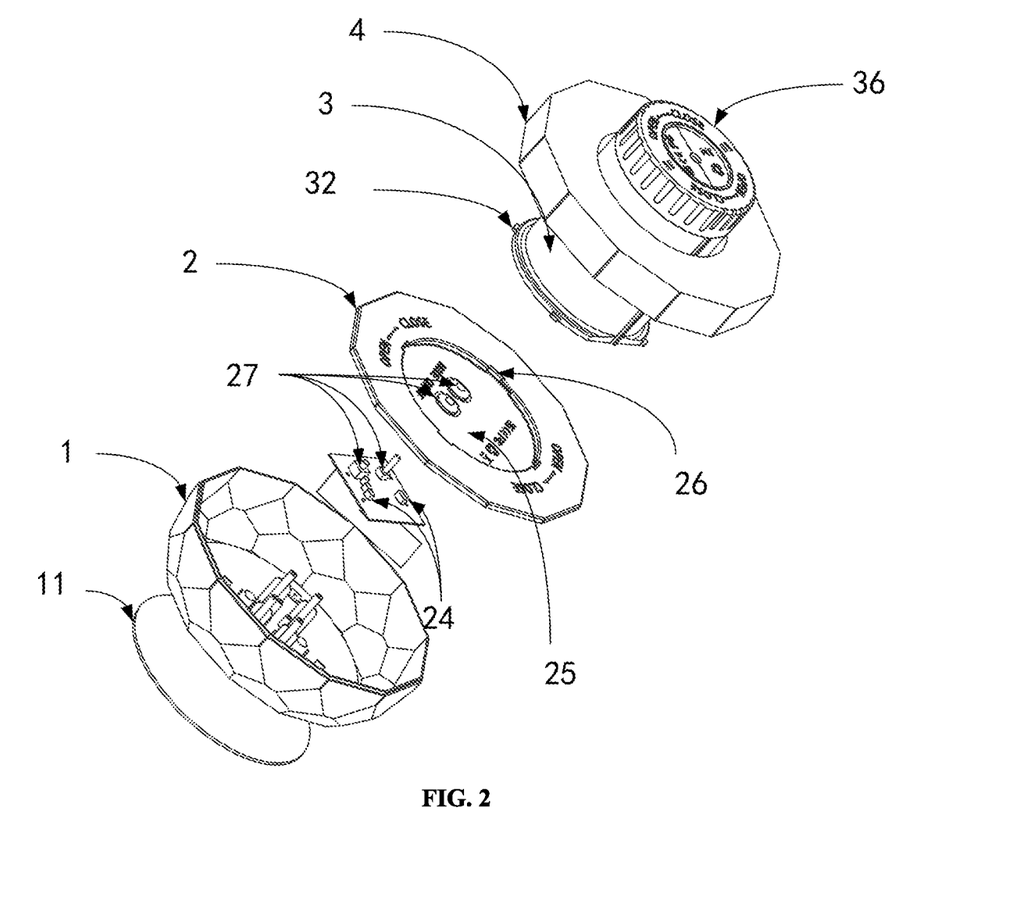
FIG. 2 is a structural exploded view in another direction in the embodiment of the present disclosure.
Figure 3:
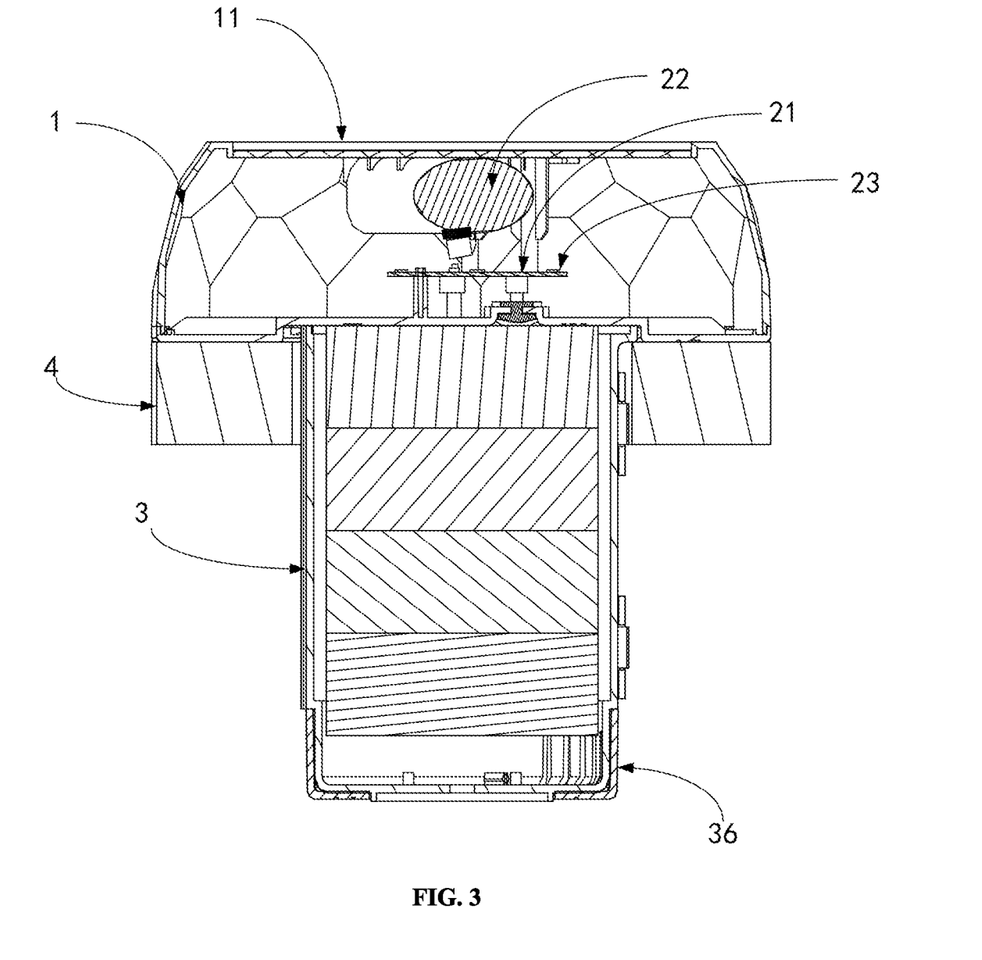
FIG. 3 is a section view in the embodiment of the present disclosure.
Figure 4:
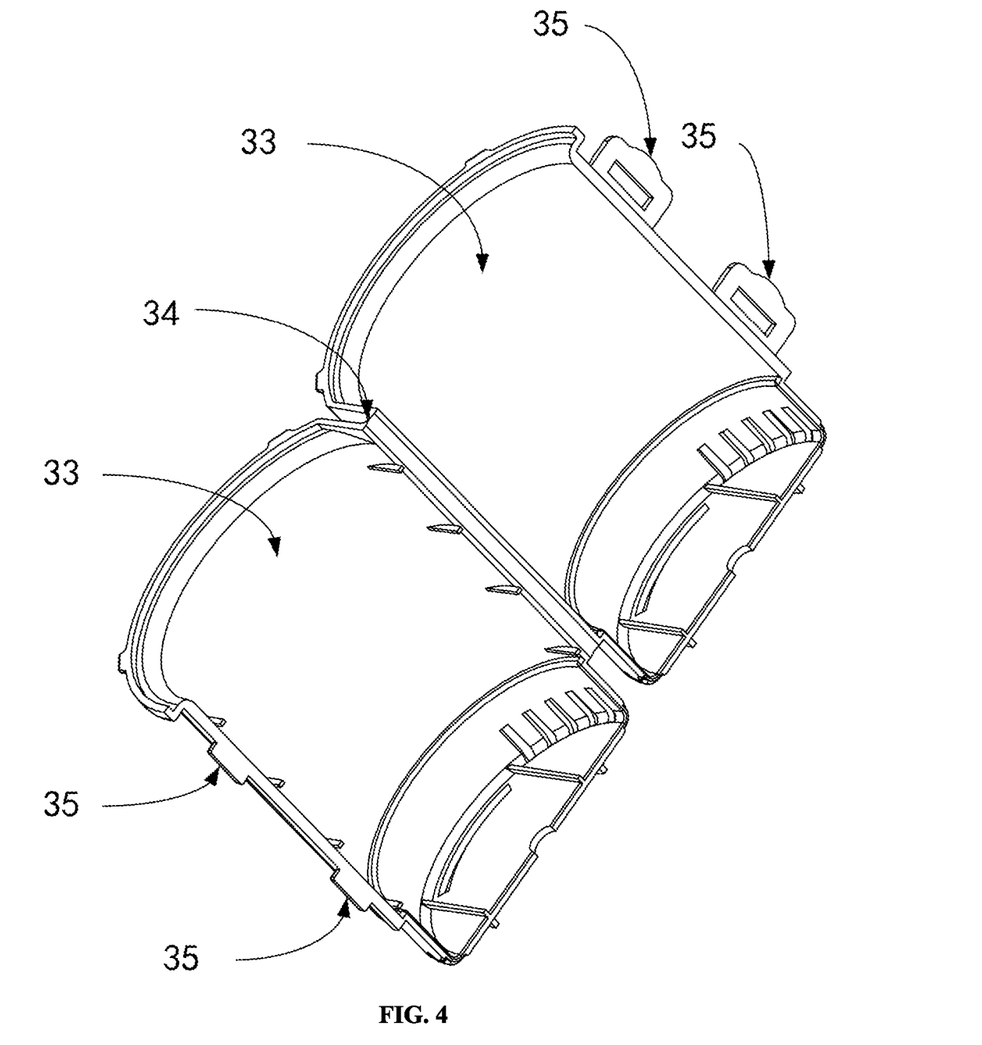
FIG. 4 is a structural schematic diagram of a cylinder in the embodiment of the present disclosure.
Figure 5:
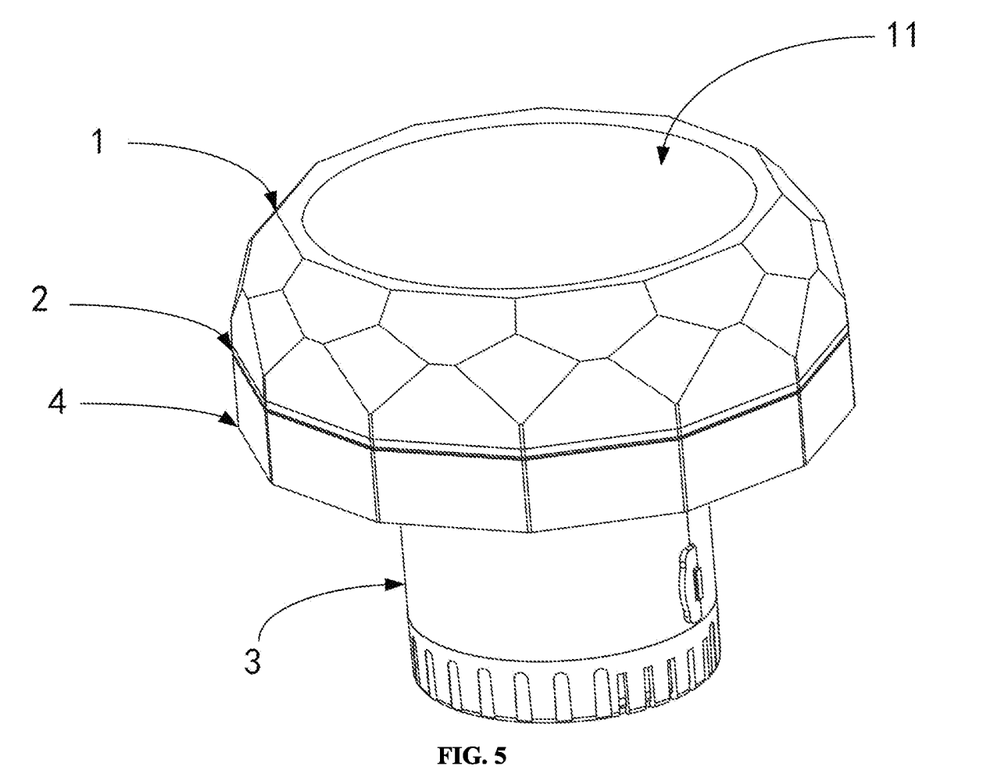
FIG. 5 is a solid structural schematic diagram in the embodiment of the present disclosure.
Figure 6:
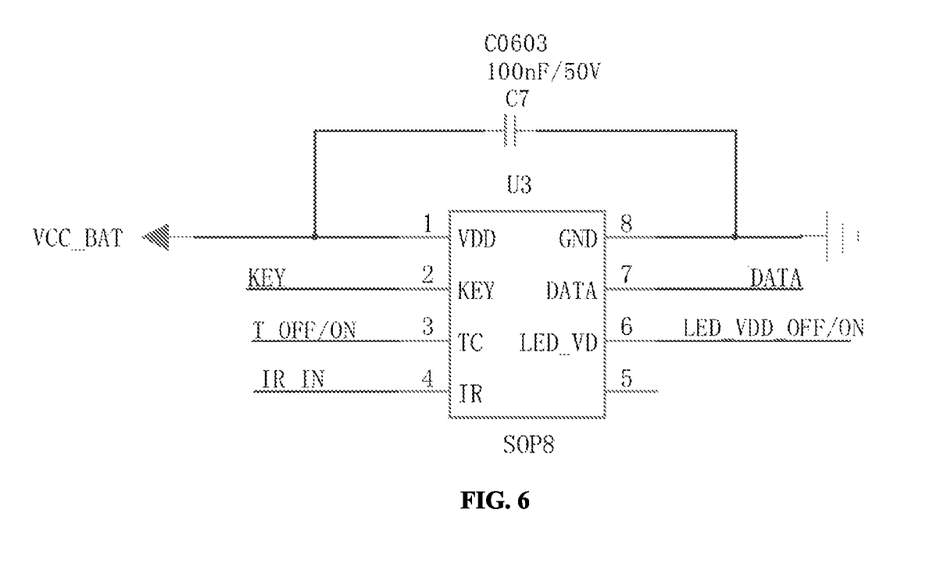
FIG. 6 is a circuit structural schematic diagram of an MCU (Micro Control Unit) on a mainboard in the embodiment of the present disclosure.
Figure 7:
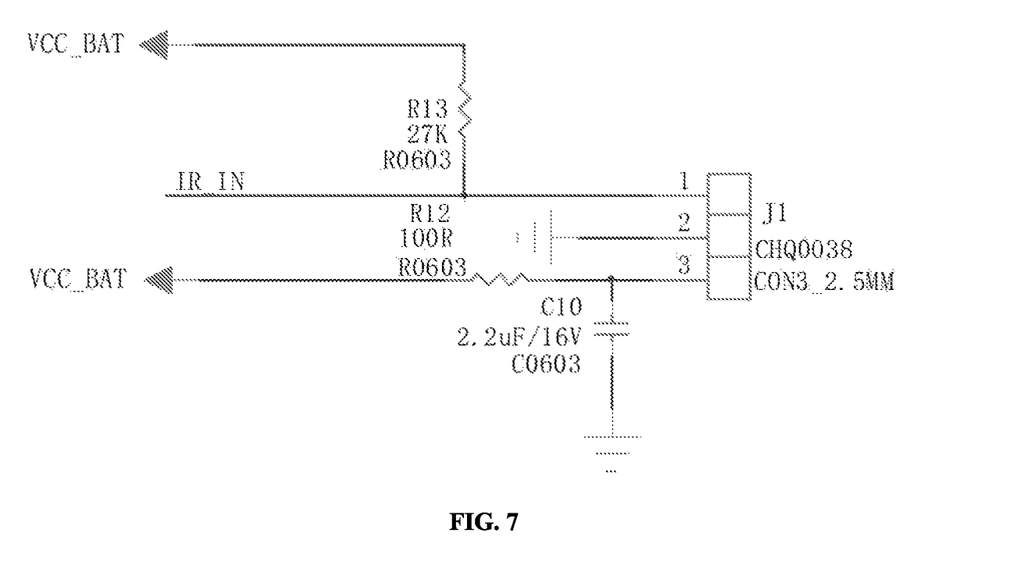
FIG. 7 is a circuit structural schematic diagram of an infrared receiving module in the embodiment of the present disclosure.
Figure 8:
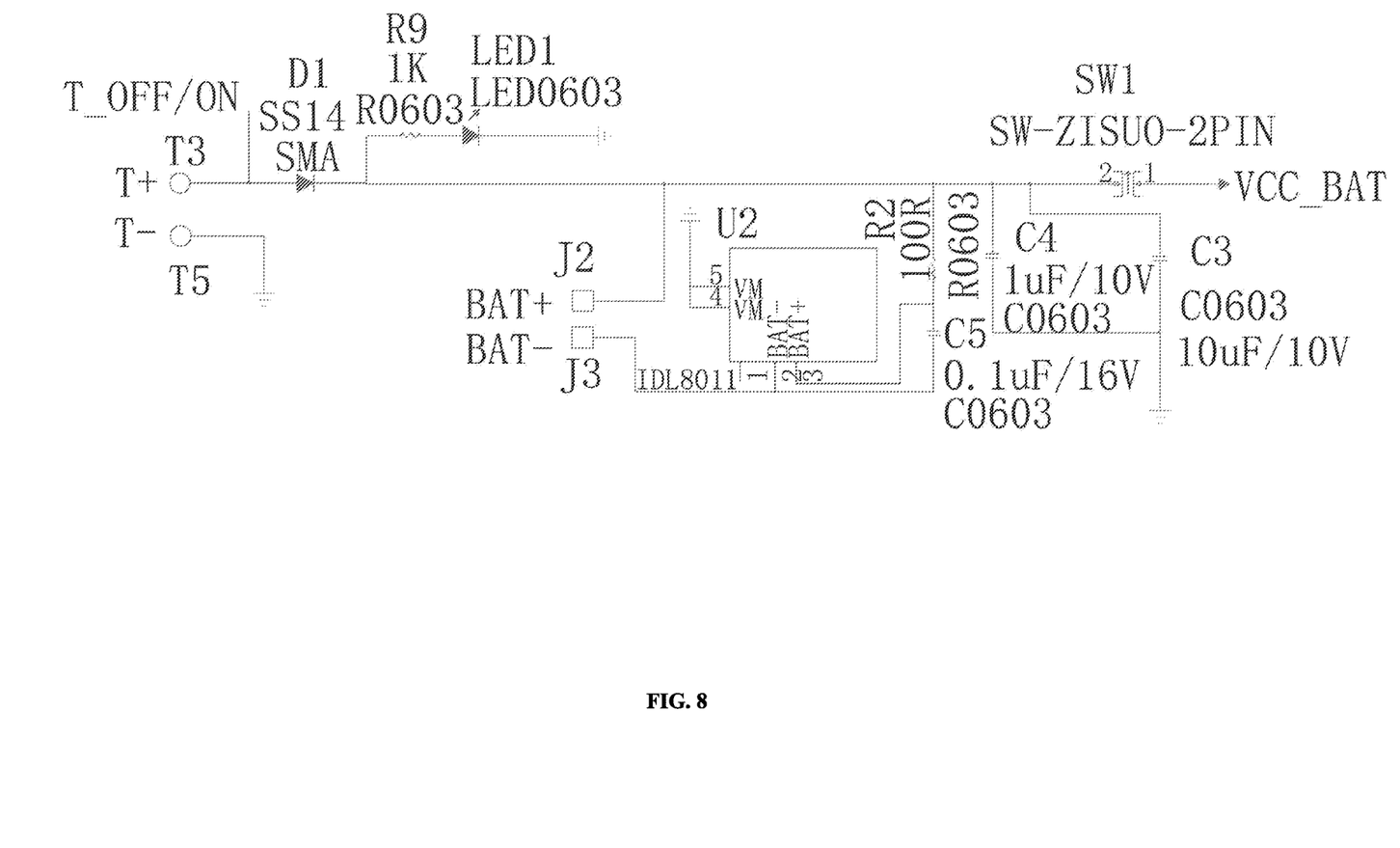
FIG. 8 is a circuit structural schematic diagram of a power management circuit in the embodiment of the present disclosure.
Figure 9:
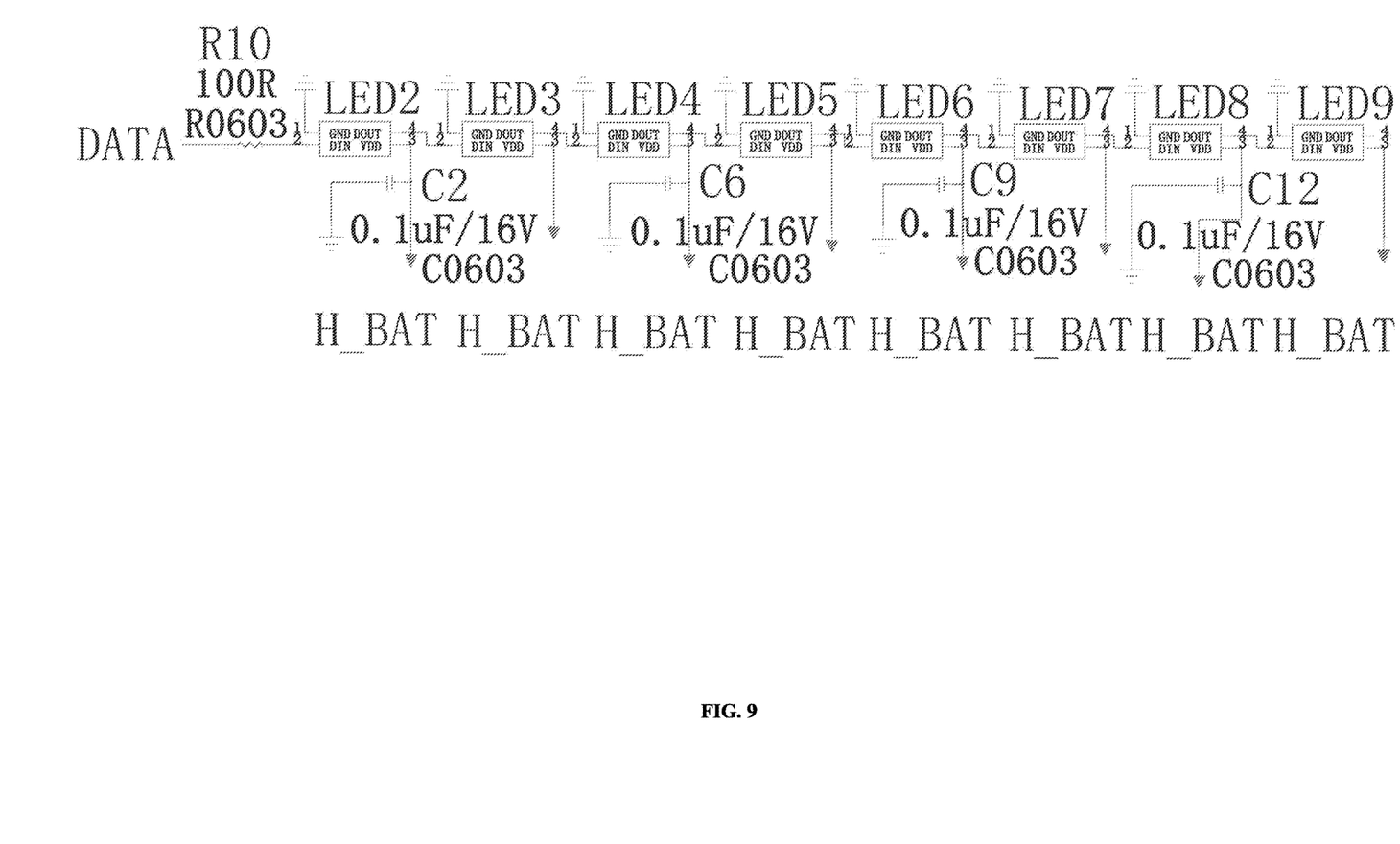
FIG. 9 is a circuit structural schematic diagram of a lamp bead in the embodiment of the present disclosure.

Further, for the structure of the cylinder 3 the cylinder 3 in the embodiment includes two semi-cylinders 33. The semi-cylinders 33 are connected through a bending part 34, and the other ends of the semi-cylinders 33 are connected through buckles 35 respectively. Moreover, lower ends of the semi-cylinder 33 are in sleeve joint with a cover body 36, and avoidance holes 37, located at the permeable holes 31, are formed in the cover body 36. The bent part 34 can be formed directly by thinning a flexible material, such as plastic.

Further, in order to improve the buoyancy force, the lampshade 1 and the base 2 are placed on the water surface. Therefore, an annular floating block 4 sleeves the cylinder 3 in the embodiment, and an upper end of the floating block 4 abuts against the bottom of the base 2, so that more slow-release chlorine tablets 100 can be placed in the cylinder 3 with the increase of the buoyancy force. Moreover, the lampshade 1 does not need to be enlarged, thus saving the volume of the buoyant lamp body, reducing the material cost, saving energy and protecting the environment. In order to prevent the floating block 4 from absorbing water, PE foam or components with the same properties as PE foam are preferentially selected for the floating block 4 in the embodiment.

Further, in order to improve the illumination effect of the lamplight, a surface of the lampshade 1 in the embodiment is provided with diamond lines 12, so that the lamplight illuminated from the lampshade 1 is more dazzling and colorful.

Further, for control buttons of the product according to the embodiment, the circuit board 21 is provided with buttons 27. The button 27 is a waterproof button. A button cap of the button 27 is placed in the mating slot 25 of the base 2. The corresponding button 27 needs to be pressed when the water is put in, and the button 27 is placed in the slot 25. After the cylinder 3 is installed, the button 27 can be hidden by the cylinder 3, so that the overall product appearance is very simple from the outside.

The above are only the preferred embodiments of the present disclosure and not intended to limit the patent scope of the present disclosure, and any equivalent structures or equivalent flow transformations based on the specification and the attached figures of the present disclosure, which is directly or indirectly applied in other related technical fields, shall similarly fall within the scope of patent protection of the present disclosure.

What is claimed is:

1. A water purification, sterilization and disinfection lamp, comprising a lampshade, a base and a cylinder for storing slow-release chlorine tablets, wherein a circuit board and a battery electrically connected with the circuit board are arranged on the base, a solar panel is installed on a surface of the lampshade, the base is covered with the lampshade to form sealed connection, the solar panel is electrically connected with the circuit board, at least one lamp bead is assembled on the circuit board, the irradiation direction of the lamp bead faces the direction of the lampshade, the cylinder is detachably installed at the bottom of the base, permeable holes are formed in the cylinder, and the slow-release chlorine tablets are in contact with the water through the permeable holes in the cylinder.

2. The water purification, sterilization and disinfection lamp according to claim 1, comprising an infrared remote controller, wherein the circuit board is integrated with infrared receiving modules for receiving infrared remote control information, and at least two infrared receiving modules are respectively located at both ends of the circuit board.

3. The water purification, sterilization and disinfection lamp according to claim 1, wherein at least two protrusions are arranged at the end, located at a cavity opening, of the cylinder, a mating slot capable of accommodating one end of the cylinder to be inserted into is arranged at the bottom of the base, an L-shaped slot is formed in a slot wall of the mating slot, an end of the cylinder is inserted into the mating slot, and the protrusions are locked into the slot by rotation.

4. The water body purifying sterilizing lamp according to claim 3, wherein the cylinder comprises two semi-cylinders, the semi-cylinders are connected through a bending part, and the other ends of the semi-cylinders are connected through buckles respectively.

5. The water permeable hole of the cover body according to claim 4, wherein lower ends of the semi-cylinder are in sleeve joint with a cover body, and avoidance holes, located at the permeable holes, are formed in the cover body.

6. The water purification, sterilization and disinfection lamp according to claim 1, wherein an annular floating block sleeves the cylinder, and an upper end of the floating block abuts against the bottom of the base.

7. The water purification, sterilization and disinfection lamp according to claim 6, wherein the floating block is PE (polyethylene) foam.

8. The water purification, sterilization and disinfection lamp according to claim 1, wherein the lamp bead is a colorful RGB (Red Green Blue) lamp bead.

9. The water purification, sterilization and disinfection lamp according to claim 1, wherein the surface of the lampshade is provided with diamond lines.

10. The water purification, sterilization and disinfection lamp according to claim 4, wherein the circuit board is provided with buttons, the button is a waterproof button, and a button cap of the button is placed in the mating slot of the base.

* * * * *